United States Patent [19]

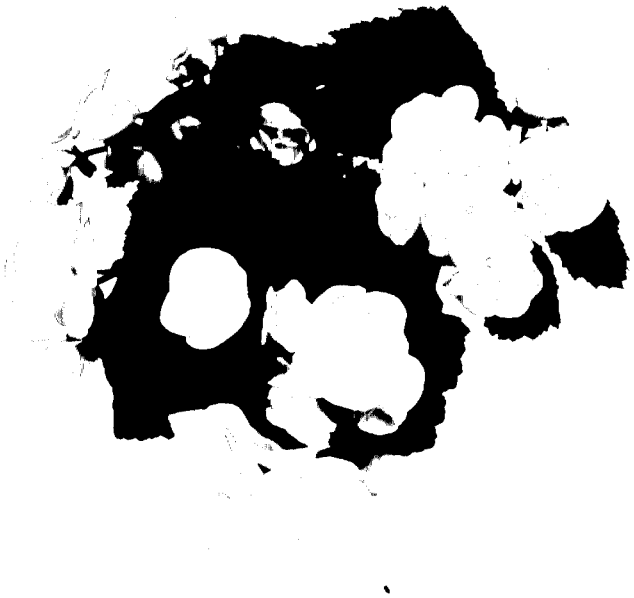

Rohde

[11] Patent Number: Plant 5,746

[45] Date of Patent: May 13, 1986

[54] BEGONIA PLANT NAMED KARITA

[75] Inventor: Hans J. Rohde, Nürtingen, Fed. Rep. of Germany

[73] Assignee: Mikkelsens, Inc., Ashtabula, Ohio

[21] Appl. No.: 652,486

[22] Filed: Sep. 20, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A begonia plant named Karita characterized by its medium pink double sterile flowers up to 5 cm. in diameter, medium size dark green crisp foliage, vigorous upright, self-branching mounded plant, year round flowering, and the ability to maintain good quality flowers for long periods of time.

1 Drawing Figure

The present invention relates to a new and distinctive cultivar of begonia plant, botanically known as *Begonia hiemalis, Fotsch,* and known by the cultivar name Karita.

The new cultivar was discovered by me as a mutation of my cultivar Kascade (unpatented) and was observed in a group of 14 cm. flowering plants of Kascade in a cultivated area. Kascade was from a cross of my tuberous begonia Rieger K-6-72×beg. Socotrana.

Asexual reproduction by stem and/or leaf cuttings has reproduced the unique features of the new cultivar through successive propagations.

The following characteristics distinguish Karita from both its parent and other begonias commercially known and used in the floriculture industry:

1. Karita is earlier flowering, freer growing, easier to propagate, and has better clear pink colored flowers than Kascade.

2. In comparison to Aphrodite Pink, disclosed in U.S. Plant Pat. No. 3,318, Karita has less tepals (average 18), more vigorous stems tending to be more upright than pendulous, and propagates more readily by leaf cuttings than Aphrodite Pink.

3. In comparison to Elfe, disclosed in U.S. Plant Pat. No. 4,125, and several mutations of Elfe, the flower color is more uniform, the plant more vigorous, propagation slower, and flowering is later for Karita than Elfe.

4. Improved Schwabenland Pink, disclosed in U.S. Plant Pat. No. 3,628, has single type flowers (4 tepals), large foliage, and more vigorous growth than Karita.

5. In comparison to Kanon, a cultivar of the present inventor disclosed in an application for U.S. Plant Patent filed simultaneous herewith and another mutation of Kascade, the flower color of Karita is lighter and flowering is earlier.

The accompanying colored photograph taken December 1983 illustrates the overall appearance of this cultivar taken as an oblique view of the plant and showing the colors as true as it is reasonably possible to obtain in a colored reproduction of this type.

The following is a detailed description of my new begonia cultivar based on plants produced under commercial practices in greenhouses in Nurtingen, West Germany and Ashtabula, Ohio, and grown in 10 cm. plastic pots. Color references are made to The Royal Horticultural Society Colour Chart except where general color terms of ordinary dictionary significance are used.

Parentage: Mutation of begonia cultivar Kascade.

Propagation:

(A) *Type cutting.*—Leaf cutting initially under plastic tents.

(B) *Time to root.*—12–15 days at 24° C. summer; 15–20 days at 24° C. winter.

(C) *Rooting habit.*—Fibrous, dendritic, and abundant.

(D) *Time for shoot development.*—For 2 cm. long shoots, 8–9 weeks in summer; 12–13 weeks in winter.

Plant description:

(A) *Form.*—Compact, closely internoded, vigorous, generally self-supporting, herbaceous.

(B) *Habit of growth.*—Upright, self-branching, rapid growth, compact dark green foliage; considered a short to medium height plant.

(C) *Foliage.*—Simple leaves that have vigorous petioles, alternate; (1) Size: 8 cm.×10 cm. on older leaves, diminishing to 4×6 cm. near flowering terminal. Specimen plants in 14 cm. pots may be upwards of 10×14 cm. (2) Shape: Generally ovate to orbicular, apice nearly acute, base unequal cordate. (3) Texture: Crisp to firm, top glabrous, underside rugose. (4) Margin: Crenulate. (5) Color: Young foliage top side, nearly yellow green 147A heavily infused with maroon; underside red purple 59A; mature foliage top side, darker than yellow green 147A or 139A, under side near green 148A with tinge of red overtone. (6) Venation: Palmate.

Flowering description:

(A) *Flowering habit.*—Flowering generally occurs in terminal racemes with the inflorescence having 6–8 flowers; once flowering begins, it continues at each succeeding node.

(B) *Natural flowering season.*—Flowering is indeterminant, with flowering occurring in all seasons.

(C) *Flower buds.*—Round to slightly oval, 15–18 mm. in diameter prior to opening with outer tepals being pink with some green at base.

(D) *Flowers borne.*—On strong self-supporting pedicels originating from vigorous peduncles giving the appearance of a strong plant.

(E) *Quantity.*—Not considered a highly floriferous cultivar, but flowers are uniformly placed to give excellent contrast between foliage and flowers.

(F) *Tepals.*—(1) Shape: Outer nearly round, inner ovate. (2) Color top side in winter when opening, red 52B-C, fading to red 48C, with center to red 38C and yellow 15A; under side red 49A. (3) Number of tepals: Average 16–18, but up to 24. (4) Size of tepals: Basal 35 mm. to interior 10 mm. (5) Flowering size: Up to 50–55 mm.

(G) *Reproductive organs.*—None, cultivar is sterile and presumed to be a triploid (4N×2N).

Disease resistance: No apparent susceptability to powdery mildew or xanthomonas, the two most common diseases.

I claim:

1. A begonia plant named Karita, as described and illustrated, having medium pink double sterile flowers up to 5 cm. in diameter; medium size dark green crisp foliage; vigorous upright, self-branching mounded plant; year round flowering, and the ability to maintain good quality flowers for long periods of time.

* * * * *